United States Patent
Maruhata (12)

(10) Patent No.: US 9,186,692 B2
(45) Date of Patent: Nov. 17, 2015

(54) PARTICLE SUPPLYING APPARATUS, METHOD OF CONTROLLING PARTICLE SUPPLYING APPARATUS, AND METHOD OF ACQUIRING SPEED DETERMINING INFORMATION

(71) Applicant: LIVEDO CORPORATION, Ehime (JP)

(72) Inventor: Kazuya Maruhata, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 216 days.

(21) Appl. No.: 14/030,421

(22) Filed: Sep. 18, 2013

(65) Prior Publication Data
US 2014/0099429 A1 Apr. 10, 2014

(30) Foreign Application Priority Data

Oct. 9, 2012 (JP) .................................. 2012-224052

(51) Int. Cl.
*B05D 1/28* (2006.01)
*B05C 5/00* (2006.01)
(Continued)

(52) U.S. Cl.
CPC ............... *B05C 5/00* (2013.01); *A61F 13/1565* (2013.01); *B05D 1/40* (2013.01); *A61F 2013/15853* (2013.01)

(58) Field of Classification Search
CPC .... B05C 1/08; A51F 13/15658; A51F 15/001
USPC ........................................ 141/12, 81; 53/205
See application file for complete search history.

(56) References Cited

U.S. PATENT DOCUMENTS

| 5,030,314 A | 7/1991 | Lang |
| 2006/0024433 A1* | 2/2006 | Blessing ........... A61F 13/15658 427/180 |
| 2011/0130732 A1 | 6/2011 | Jackels et al. |

(Continued)

FOREIGN PATENT DOCUMENTS

| CN | 102647968 | 8/2012 |
| EP | 2 119 420 | 11/2009 |

(Continued)

OTHER PUBLICATIONS

Extended European Search Report issued Nov. 25, 2013 in corresponding European patent application No. 13004603.0.

*Primary Examiner* — Xiao Zhao
(74) *Attorney, Agent, or Firm* — Wenderoth, Lind & Ponack, L.L.P.

(57) ABSTRACT

In an absorbent sheet manufacturing apparatus, a storage part stores speed determining information including relationships between conveying speed of a first sheet member and rotational speed of a supply cylinder and corresponding respectively to target particle densities. A control part determines the rotational speed of the supply cylinder on the basis of a target particle density, the conveying speed and the speed determining information. Even if various changes are made to the conveying speed of the first sheet member, the amount of particles supplied can be accurately controlled such that the density of particles on the first sheet member matches the target particle density. Even if various changes are made to the target particle density, the amount of particles supplied can be accurately controlled in consideration of the conveying speed such that the density of particles matches the target particle density.

4 Claims, 8 Drawing Sheets

(51) Int. Cl.
*A61F 13/15* (2006.01)
*B05D 1/40* (2006.01)

(56) References Cited

U.S. PATENT DOCUMENTS

2012/0312463 A1 12/2012 Ogasawara et al.
2013/0087289 A1 4/2013 Ogasawara et al.

FOREIGN PATENT DOCUMENTS

| | | |
|---|---|---|
| EP | 2 329 803 | 6/2011 |
| EP | 2 491 908 | 8/2012 |
| FR | 2 583 377 | 12/1986 |
| JP | 2000-327127 | 11/2000 |
| WO | 2011/048964 | 4/2011 |
| WO | 2013/008430 | 1/2013 |
| WO | 2013/008431 | 1/2013 |

* cited by examiner

PARTICLE SUPPLYING APPARATUS, METHOD OF CONTROLLING PARTICLE SUPPLYING APPARATUS, AND METHOD OF ACQUIRING SPEED DETERMINING INFORMATION

TECHNICAL FIELD

The present invention relates to a particle supplying apparatus for supplying particles of an absorbent material or a deodorant material onto a sheet member, a method of controlling the particle supplying apparatus, and a method of acquiring speed determining information for use in the particle supplying apparatus.

BACKGROUND ART

Conventionally, absorbent articles such as absorbent pads for light incontinence that are used in disposable diapers by being attached to the inner sides of the diapers use an absorbent sheet in which particles of a highly absorbent resin or the like are sandwiched between and fixed to two sheet members of nonwoven fabric or the like. In manufacturing of such an absorbent sheet, particles of the highly absorbent resin are supplied onto one of the sheet members that is being conveyed at a constant speed, and then the other sheet member is placed on and bonded to the sheet member being conveyed.

In a manufacturing apparatus disclosed in Japanese Patent Application Laid-Open No. 2000-327127 (Document 1), a garnet cylinder that supplies pulp fiber is provided above absorbent paper that is running with a mesh belt. The garnet cylinder has saw teeth in its circumference surface. Rotation of the garnet cylinder causes the saw teeth to scrape pulp fiber that is fed from a supply belt by a predetermined amount. The scraped pulp fiber is moved downward by the rotation of the garnet cylinder and supplied onto the running absorbent paper.

With the manufacturing apparatus of Document 1, however, if the number of revolutions of a servomotor on the supply belt increases in proportion to the running speed of the mesh belt, the amount of the pulp fiber to be supplied will not increase in proportion to the running speed of the mesh belt in a region where the running speed of the mesh belt is high, and accordingly will be less than the expected amount that is determined on the assumption that the amount of pulp fiber supplied increases in proportion to the running speed.

In view of this, the manufacturing apparatus of Document 1 controls the number of revolutions of the servomotor on the supply belt independently of the running speed of the mesh belt such that the supply curve of the pulp fiber is proportional to the running speed of the mesh belt. Document 1, however, discloses a technique for controlling the supply belt or the like, assuming a manufacturing apparatus in which the garnet cylinder is provided with, for example, a screw and the supply belt for supplying pulp fiber or the like. It thus has failed to disclose a technique of control performed by apparatuses with other configurations.

SUMMARY OF INVENTION

The present invention is intended for a particle supplying apparatus for supplying particles of an absorbent material or a deodorant material onto a sheet member, and it is an object of the present invention to accurately control the amount of particles supplied. The present invention is also intended for a method of controlling the particle supplying apparatus and a method of acquiring speed determining information for use in the particle supplying apparatus.

A particle supplying apparatus according to the present invention supplies particles of an absorbent material or a deodorant material onto a sheet member. The particle supplying apparatus includes a supply cylinder having a cylinder outer side surface having a plurality of recessed supply portions arranged in a circumferential direction, a particle replenishment part located above the supply cylinder, containing particles of an absorbent material or a deodorant material, and for successively replenishing the plurality of recessed supply portions with the particles through a particle replenishment opening that faces the cylinder outer side surface, a sheet conveying mechanism located below the supply cylinder and for conveying a sheet member that is a continuous sheet in a predetermined conveyance direction, a cylinder rotation mechanism for rotating the supply cylinder about a cylinder rotational axis extending in a horizontal direction and bringing a lower portion of the cylinder outer side surface and the sheet member into contact with or close proximity to each other so as to successively supply the particles from the plurality of recessed supply portions onto the sheet member, a storage part for storing speed determining information that includes a plurality of relationships between conveying speed of the sheet member and rotational speed of the supply cylinder and corresponding respectively to a plurality of target particle densities that are target densities of the particles on the sheet member, an input part, and a control part for determining a rotational speed of the supply cylinder on the basis of a target particle density and a conveying speed of the sheet member that are input from the input part and the speed determining information stored in the storage part. The particle supplying apparatus makes it possible to accurately control the amount of particles supplied.

In a preferred embodiment of the present invention, the speed determining information includes, for each of a plurality of types of particles, a plurality of relationships between conveying speed of the sheet member and rotational speed of the supply cylinder and corresponding respectively to the plurality of target particle densities.

In another preferred embodiment of the present invention, in each of the plurality of relationships between conveying speed of the sheet member and rotational speed of the supply cylinder, a ratio of an increase in the rotational speed of the supply cylinder to an increase in the conveying speed of the sheet member gradually increases with an increase in the conveying speed of the sheet member.

In a method of controlling a particle supplying apparatus according to the present invention, the particle supplying apparatus includes a supply cylinder having a cylinder outer side surface having a plurality of recessed supply portions arranged in a circumferential direction, a particle replenishment part located above the supply cylinder, containing particles of an absorbent material or a deodorant material, and for successively replenishing the plurality of recessed supply portions with the particles through a particle replenishment opening that faces the cylinder outer side surface, a sheet conveying mechanism located below the supply cylinder and for conveying a sheet member that is a continuous sheet in a predetermined conveyance direction, and a cylinder rotation mechanism for rotating the supply cylinder about a cylinder rotational axis extending in a horizontal direction and bringing a lower portion of the cylinder outer side surface and the sheet member into contact with or close proximity to each other so as to successively supply the particles from the plurality of recessed supply portions onto the sheet member. The method of controlling the particle supplying apparatus includes a) storing speed determining information that includes a plurality of relationships between conveying speed of the sheet member and rotational speed of the supply cylinder and corresponding respectively to a plurality of target particle densities that are target densities of the particles on the sheet member, b) inputting a target particle density and a conveying speed of the sheet member, and c) determining a rotational speed of the supply cylinder on the basis of the target particle density and the conveying speed that are input in the operation b) and the speed determining information stored in the operation a). This control method makes it possible to accurately control the amount of particles supplied.

In a method of acquiring speed determining information for use in a particle supplying apparatus according to the present invention, the particle supplying apparatus includes a supply cylinder having a cylinder outer side surface having a plurality of recessed supply portions arranged in a circumferential direction, a particle replenishment part located above the supply cylinder, containing particles of an absorbent material or a deodorant material, and for successively replenishing the plurality of recessed supply portions with the particles through a particle replenishment opening that faces the cylinder outer side surface, a sheet conveying mechanism located below the supply cylinder and for conveying a sheet member that is a continuous sheet in a predetermined conveyance direction, a cylinder rotation mechanism for rotating the supply cylinder about a cylinder rotational axis extending in a horizontal direction and bringing a lower portion of the cylinder outer side surface and the sheet member into contact with or close proximity to each other so as to successively supply the particles from the plurality of recessed supply portions onto the sheet member, a storage part for storing speed determining information that includes a relationship between conveying speed of the sheet member and rotational speed of the supply cylinder and corresponding to a target particle density that is a target density of the particles on the sheet member, an input part, and a control part for determining a rotational speed of the supply cylinder on the basis of a conveying speed of the sheet member that is input from the input part and the speed determining information stored in the storage part. The method of acquiring speed determining information includes a) acquiring an amount of particles supplied from the supply cylinder to the sheet member per unit time for each of a plurality of rotational speeds of the supply cylinder so as to acquire rotational-speed vs. particle-supply-amount information, b) obtaining an amount of particles that is necessary to be supplied from the supply cylinder per unit time in order to attain the target particle density for each of a plurality of conveying speeds of the sheet member so as to acquire conveying-speed vs. particle-supply-amount information, and c) obtaining a relationship between conveying speed and rotational speed and corresponding to the target particle density on the basis of the rotational-speed vs. particle-supply-amount information and the conveying-speed vs. particle-supply-amount information.

These and other objects, features, aspects and advantages of the present invention will become more apparent from the following detailed description of the present invention when taken in conjunction with the accompanying drawings.

DESCRIPTION OF EMBODIMENTS

Figure 1:
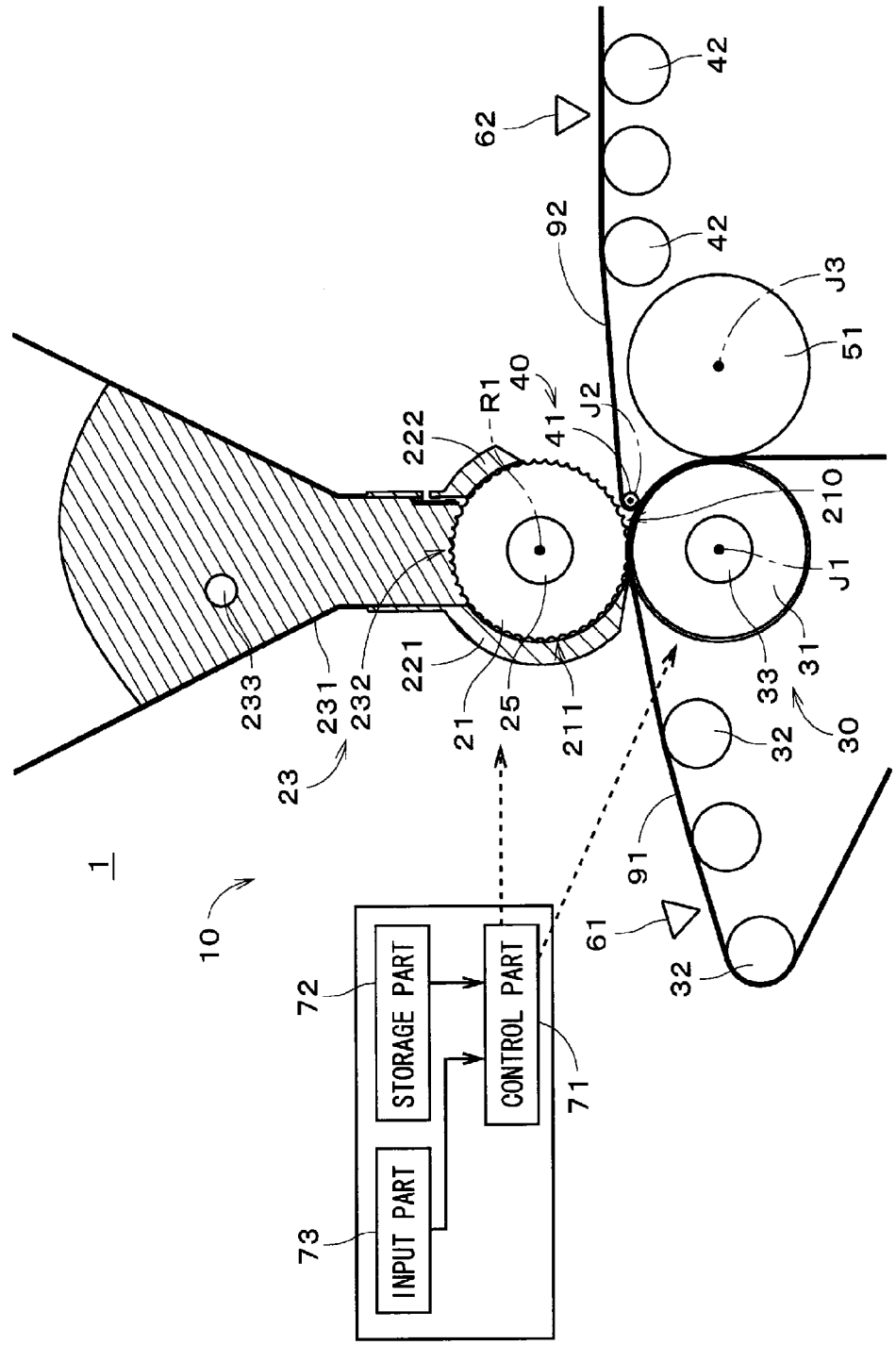
FIG. 1 illustrates a configuration of an absorbent sheet manufacturing apparatus according to an embodiment of the present invention.

FIG. 1 illustrates a configuration of an absorbent sheet manufacturing apparatus 1 according to an embodiment of the present invention. The absorbent sheet manufacturing apparatus 1 is a sheet member manufacturing apparatus for manufacturing absorbent sheets for absorbent articles by sandwiching particles of an absorbent material between sheet members of nonwoven fabric or the like. In the present embodiment, particles of a highly absorbent resin such as a super absorbent polymer (SAP) are used as particles of the absorbent material. The absorbent sheets are absorbent-article sheet members that are used for absorbent articles such as disposable diapers and absorbent pads for light incontinence.

The absorbent sheet manufacturing apparatus 1 includes a supply cylinder 21 that is a generally cylindrical member centered about a cylinder rotational axis R1 extending in a horizontal direction, a first sheet conveying roller 31 having a generally columnar shape centered about a first central axis J1 parallel to a direction in which the cylinder rotational axis R1 extends (hereinafter, referred to as an "axial direction"), a second sheet conveying roller 41 having a generally columnar shape centered about a second central axis J2 parallel to the axial direction, and a bonding roller 51 having a generally columnar shape centered about a third central axis J3 parallel to the axial direction. The first central axis J1 is located vertically below the cylinder rotational axis R1. The absorbent sheet manufacturing apparatus 1 further includes a plurality of auxiliary rollers 32 and 42, each having a generally columnar shape centered about a central axis parallel to the axial direction, and first and second application parts 61 and 62 for applying an adhesive (in the present embodiment, a hot-melt adhesive).

The absorbent sheet manufacturing apparatus 1 further includes a cylinder rotation mechanism 25 for rotating the supply cylinder 21 about the cylinder rotational axis R1, a first roller rotation mechanism 33 for rotating the first sheet conveying roller 31 about the first central axis J1, a control part 71 for controlling these rotation mechanisms, a storage part 72 for storing various types of information, and an input part 73 that is used to input information.

The supply cylinder 21 is rotated in the counterclockwise direction in FIG. 1 by the cylinder rotation mechanism 25. The supply cylinder 21 supplies highly absorbent resin particles (hereinafter, simply referred to as "particles") onto a first sheet member 91 in the vicinity of its lowermost portion, the first sheet member 91 being a continuous sheet formed of nonwoven fabric or the like. The first sheet conveying roller 31 is rotated in the clockwise direction in FIG. 1 by the first roller rotation mechanism 33 and conveys the first sheet member 91 to the vicinity of the lowermost portion of the supply cylinder 21. The first sheet conveying roller 31 and the first roller rotation mechanism 33 constitute a sheet conveying mechanism for conveying the first sheet member 91 in a predetermined conveyance direction (i.e., from the left to the right in FIG. 1) below the supply cylinder 21. Hereinafter, the first sheet conveying roller 31 and the first roller rotation mechanism 33 are collectively referred to as a "first sheet conveying mechanism 30."

The second sheet conveying roller 41 is rotated in the counterclockwise direction in FIG. 1 by a second roller rotation mechanism (not shown) in synchronization with the rotation of the first sheet conveying roller 31 and conveys a second sheet member 92 to the vicinity of the lowermost portion of the supply cylinder 21, the second sheet member 92 being a continuous sheet formed of nonwoven fabric or the like. The second sheet conveying roller 41 and the second roller rotation mechanism constitute a second sheet conveying mechanism 40 for conveying the second sheet member 92 in a predetermined conveyance direction. The conveying speed of the second sheet member 92 by the second sheet conveying mechanism 40 is equal to that of the first sheet member 91 by the first sheet conveying mechanism 30.

The bonding roller 51 and the auxiliary rollers 42 rotate in the counterclockwise direction in FIG. 1, whereas the first sheet conveying roller 31 and the auxiliary rollers 32 rotate in the clockwise direction in FIG. 1. The first application part 61 is disposed above the auxiliary rollers 32 and applies an adhesive to the first sheet member 91. The second application part 62 is disposed above the auxiliary rollers 42 and applies an adhesive to the second sheet member 92. The bonding roller 51 is a sheet bonding part disposed beside the first sheet conveying roller 31 and for bonding the first sheet member 91 and the second sheet member 92 by bringing the two sheet members together so that the sheet members are sandwiched between the bonding roller 51 and the first sheet conveying roller 31.

Above the supply cylinder 21 is disposed a particle replenishment part 23. The particle replenishment part 23 includes a particle tank 231 that is disposed above the supply cylinder 21 and for holding particles of the highly absorbent resin, and a level sensor 233 provided in the particle tank 231. When the level sensor 233 has detected that the amount of particles in the particle tank 231 decreased to a certain amount or less, the particle tank 231 is replenished with particles. The particle tank 231 extends in a direction approximately parallel to the direction of gravity and has a particle replenishment opening 232 at its low end, the particle replenishment opening 232 facing a cylinder outer side surface 211 that is the outer side surface of the supply cylinder 21. The particle replenishment opening 232 faces an area including the uppermost portion of the supply cylinder 21.

Around the supply cylinder 21 are provided a first cover part 221 for covering part of the cylinder outer side surface 211 of the supply cylinder 21 and a second cover part 222 for covering another part of the cylinder outer side surface 211. The first cover part 221 extends from the particle replenishment opening 232 in the rotation direction of the supply cylinder 21 (i.e., the counterclockwise direction in FIG. 1) to the vicinity of the lowermost portion of the supply cylinder 21 and covers the cylinder outer side surface 211 on the left side of the supply cylinder 21. The second cover part 222 extends from the particle replenishment opening 232 in the direction opposite to the rotation direction of the supply cylinder 21 (i.e., the clockwise direction in FIG. 1 that is reverse to the rotation direction) to the vicinity of the right edge part of the supply cylinder 21 and covers the cylinder outer side surface 211 on the right side of the supply cylinder 21.

Of the cylinder outer side surface 211 of the supply cylinder 21, a region extending from the lower end of the first cover part 221 to the lower end of the second cover part 222, that is, a region exposed from the first cover part 221 and the second cover part 222 on the lower side of the supply cylinder 21 is a particle supply region 210, which will be described later. The first cover part 221 extends in the clockwise direction from the particle supply region 210, and the second cover part 222 extends in the counterclockwise direction from the particle supply region 210.

Figure 2:
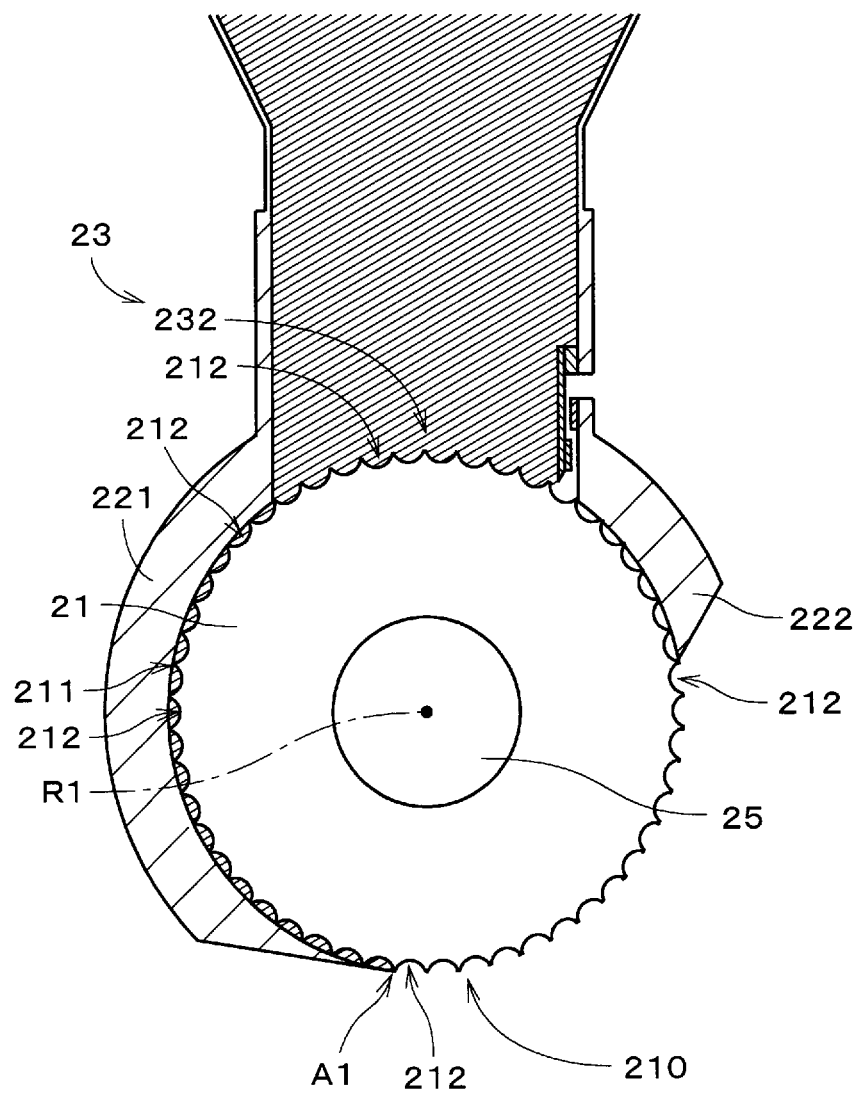
FIG. 2 is a cross-sectional view showing the vicinity of a supply cylinder.
Figure 3:
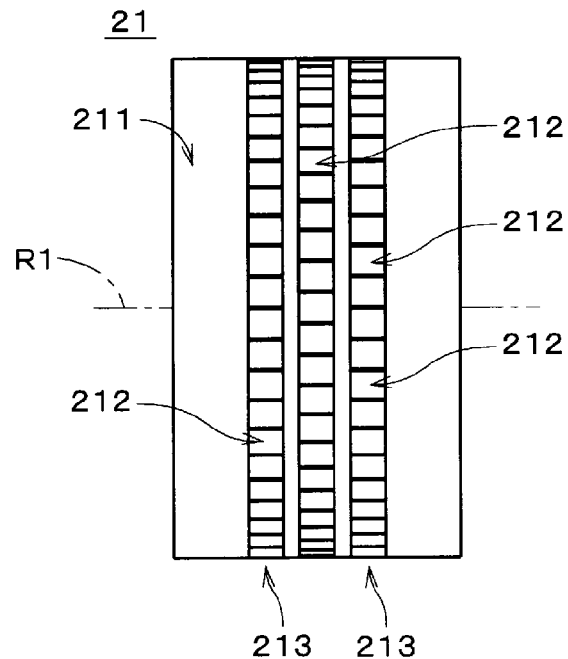
FIG. 3 is a front view of the supply cylinder.

FIG. 2 is an enlarged cross-sectional view showing the vicinity of the supply cylinder 21. FIG. 2 shows a cross section taken along a plane perpendicular to the cylinder rotational axis R1. FIG. 3 shows the cylinder outer side surface 211 of the supply cylinder 21 when viewed in a direction perpendicular to the cylinder rotational axis R1. In FIG. 2, particles are hatched with fine parallel diagonal lines. The first cover part 221 and the second cover part 222 are not shown in FIG. 3.

The cylinder outer side surface 211 of the supply cylinder 21 has a plurality of recessed supply portions 212 arranged respectively at a plurality of positions in the axial direction as shown in FIGS. 2 and 3, the recessed supply portions 212 being close to each other in a circumferential direction centered about the cylinder rotational axis R1. A plurality of recessed supply portions 212 that are arranged in the circumferential direction at a position in the axial direction are collectively referred to as a recess line 213. As shown in FIG. 3, the supply cylinder 21 has three recess lines 213. In the present embodiment, each recessed supply portion 212 has a generally rectangular shape when viewed in a direction perpendicular to the cylinder rotational axis R1 and has a generally arcuate bottom surface shape as shown in FIG. 2 when viewed in a cross section taken along a plane perpendicular to the plane cylinder rotational axis R1. The recessed supply portions 212, however, may be of various shapes and may, for example, be of a generally rectangular shape when viewed in a cross section taken along a plane perpendicular to the cylinder rotational axis R1. The number of recess lines 213 formed in the cylinder outer side surface 211 may be one, two, or four or more.

The cylinder outer side surface 211 of the supply cylinder 21 is very close to or substantially in contact with the inner side surfaces of the first cover part 221 and the second cover part 222 at portions other than the recessed supply portions 212.

With the absorbent sheet manufacturing apparatus 1, the supply cylinder 21 rotates at high speed about the cylinder rotational axis R1, and the recessed supply portions 212 that pass through the particle replenishment opening 232 are successively replenished with particles supplied from the particle tank 231 of the particle replenishment part 23 by the force of gravity.

With the absorbent sheet manufacturing apparatus 1, the recessed supply portions 212 replenished with particles are closed by the first cover part 221 (i.e., the recessed supply portions 212 are covered on the cylinder outer side surface 211 side) during the time until the recessed supply portions 212 reach the particle supply region 210 located in the lower portion of the supply cylinder 21. When the recessed supply portions 212 pass through the particle supply region 210 beyond the edge of the first cover part 221 in the vicinity of the lowermost portion of the supply cylinder 21, i.e., the front-side edge of the first cover part 221 in the rotation direction of the supply cylinder 21, the particles in the recessed supply portions 212 are ejected out of the supply cylinder 21 and supplied onto the first sheet member 91 (see FIG. 1).

Specifically, the ejection of the particles starts immediately after the recessed supply portions 212 cross the above edge of the first cover part 221. In the following description, the position of the above edge is referred to as an "ejection start position A1." The ejection start position A1 is located posterior to (upstream of) the lowermost portion of the supply cylinder 21 in the rotation direction of the supply cylinder 21 in the vicinity of the lowermost portion of the supply cylinder 21. Since, as described previously, the supply cylinder 21 is rotated at high speed by the cylinder rotation mechanism 25, particles are ejected from each of the recessed supply portions 212 substantially along a line tangent to the cylinder outer side surface 211 at the ejection start position A1.

As described above, with the absorbent sheet manufacturing apparatus 1, the lower portion of the cylinder outer side surface 211 and the first sheet member 91 are brought into contact with or close proximity to each other by the rotation of the supply cylinder 21 by the cylinder rotation mechanism 25 and the particles are successively supplied from the recessed supply portions 212 onto the first sheet member 91. The recessed supply portions 212 that have supplied the particles to the first sheet member 91 pass through the particle supply region 210 and then, with the recessed supply portions 212 being closed by the second cover part 222, move toward the upper portion of the supply cylinder 21 to the particle replenishment opening 232 of the particle replenishment part 23.

Figure 4:
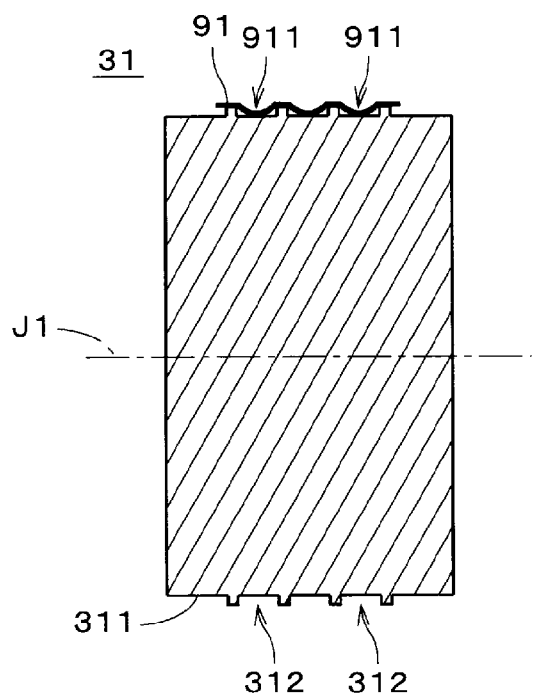
FIG. 4 is a cross-sectional view of a first sheet conveying roller.

FIG. 4 is a cross-sectional view of the first sheet conveying roller 31 and shows a cross section taken along a plane that includes the cylinder rotational axis R1 of the supply cylinder 21 and the first central axis J1 of the first sheet conveying roller 31 in FIG. 1. The first sheet conveying roller 31 has an outer side surface 311 that is a generally cylindrical surface centered about the first central axis J1. The outer side surface 311 has a plurality of annular grooves 312 formed respectively at a plurality of positions in the axial direction, the annular grooves 312 extending in the circumferential direction centered about the first central axis J1. The annular grooves 312 are disposed at the same positions in the axial direction as the recess lines 213 (see FIG. 3) of the supply cylinder 21.

The first sheet member 91 is guided to the first sheet conveying roller 31 by the auxiliary rollers 32 (see FIG. 1). At this time, the first application part 61 applies an adhesive to a plurality of strip-like (or linear) regions of the first sheet member 91 that correspond to the annular grooves 312. The strip-like regions (hereinafter, referred to as "adhesive-applied regions") are located at the same positions in the axial direction as the recess lines 213 of the supply cylinder 21 and the annular grooves 312. As described above, the first sheet member 91 is conveyed in the same direction as the direction of movement of the cylinder outer side surface 211 of the supply cylinder 21 (i.e., to the right in FIG. 1) by the first sheet conveying mechanism 30 below the ejection start position A1 (see FIG. 2) of the particle supply region 210. The particles are ejected from the supply cylinder 21 toward the adhesive-applied regions of the first sheet member 91 and are held on the first sheet member 91.

The outer side surface 311 of the first sheet conveying roller 31 has a relatively large diameter, and portions 911 of the first sheet member 91 that correspond to the annular grooves 312 are shaped into recesses extending toward the bottom of the annular grooves 312 by the first sheet member 91 being stretched by a certain tension along the outer side surface 311. In other words, the groove portions 911 corresponding to the annular grooves 312 are formed in the first sheet member 91. Because, as described above, the annular grooves 312 of the first sheet conveying roller 31 are located at the same positions as the recess lines 213 in the axial direction, most particles ejected from the recessed supply portions 212 travel toward the groove portions 911 and are held within the groove portions 911. At this time, even if particles spatter within the groove portions 911, the side walls of the groove portions 911 suppress scattering of the particles out of the groove portions 911. Besides, the aforementioned adhesive-applied regions of the first sheet member 91, which are located at the same positions as the groove portions 911, allow such particles to be easily caught within the groove portions 91.

Figure 5:
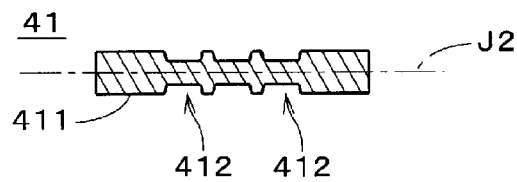
FIG. 5 is a cross-sectional view of a second sheet conveying roller.

FIG. 5 is a cross-sectional view of the second sheet conveying roller 41 and shows a cross section taken along a plane that includes the second central axis J2 of the second sheet conveying roller 41 in FIG. 1. The second sheet conveying roller 41 has an outer side surface 411 that is a generally cylindrical surface centered about the second central axis J2. The outer side surface 411 has annular grooves 412 formed respectively at a plurality of positions in the axial direction, the annular grooves 412 extending in the circumferential direction centered about the second central axis J2. The annular grooves 412 are disposed at the same positions as the positions of the recess lines 213 of the supply cylinder 21 and the annular grooves 312 of the first sheet conveying roller 31 in the axial direction.

The second sheet member 92 is guided to the second sheet conveying roller 41 by the auxiliary rollers 42 (see FIG. 1). At this time, the second application part 62 applies an adhesive to a plurality of strip-like (or linear) adhesive-applied regions of the second sheet member 92 that correspond to the annular grooves 412. The adhesive-applied regions are located at the same positions as the recess lines 213 of the supply cylinder 21 and the annular grooves 312 of the first sheet conveying roller 31 in the axial direction. Some of the particles ejected from the recessed supply portions 212 of the supply cylinder 21 spatter within the groove portions 911 (see FIG. 4) of the first sheet member 91 and travel toward the second sheet conveying roller 41, and some of the particles travel from the recessed supply portions 212 of the supply cylinder 21 directly to the second sheet conveying roller 41.

Figure 6:
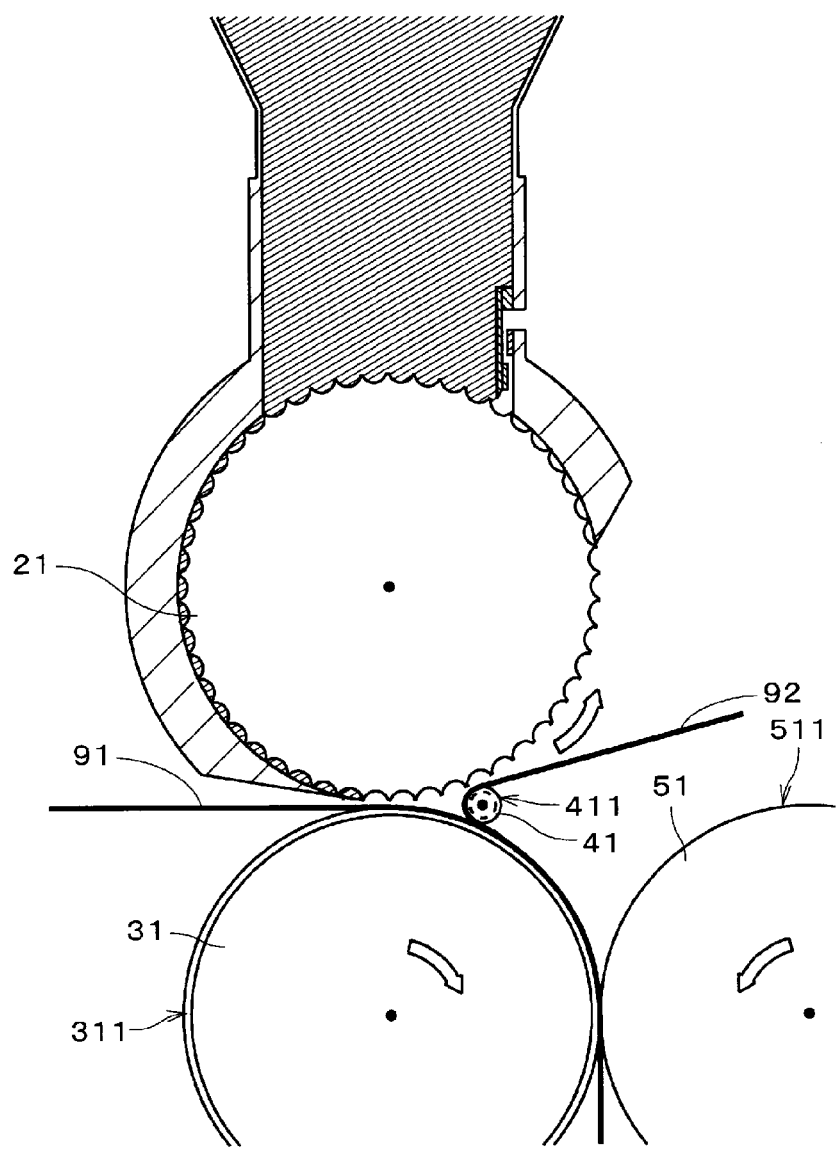
FIG. 6 shows the vicinity of the supply cylinder.

As described above, the annular grooves 412 of the second sheet conveying roller 41 are located at the same positions as the recess lines 213 and the annular grooves 312 in the axial direction. Thus, the particles traveling toward the second sheet conveying roller 41 collide with portions of the second sheet member 92 above the annular grooves 412 (i.e., portions at which the back surface of the second sheet member 92 is not in contact with any member). This absorbs the shock of the collision and allows the particles to be held in the groove portions 911 of the first sheet member 91. The second sheet member 92 is conveyed along the outer side surface 411 of the second sheet conveying roller 41 as shown in FIG. 6 and is brought together with the first sheet member 91 that has passed under the lowermost portion of the supply cylinder 21.

Figure 7:
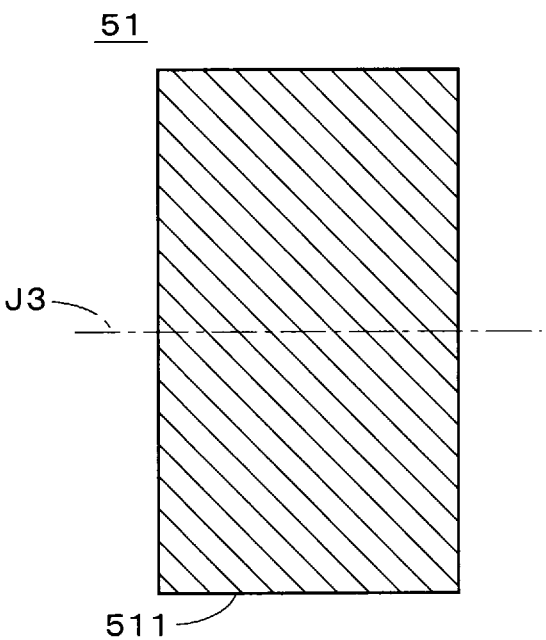
FIG. 7 is a cross-sectional view of a bonding roller.

FIG. 7 is a cross-sectional view of the bonding roller 51 and shows a cross section taken along a plane that includes the third central axis J3 of the bonding roller 51 in FIG. 1. The bonding roller 51 has an outer side surface 511 that is a cylindrical surface centered about the third central axis J3. The outer side surface 511 is a flat surface. As shown in FIG. 6, the first sheet member 91 to which particles have been supplied and the second sheet member 92 on the first sheet member 91 are sandwiched between the outer side surface 311 of the first sheet conveying roller 31 and the outer side surface 511 of the bonding roller 51. Both (or either) of the first sheet conveying roller 31 and the bonding roller 51 are provided with a heater. In the first sheet member 91 and the second sheet member 92, regions that are in contact with raised portions on both sides of each annular groove 312 (see FIG. 4) of the outer side surface 311 of the first sheet conveying roller 31 are sealed by heat so that the first sheet member 91 and the second sheet member 912 are bonded to each other.

Figure 8:
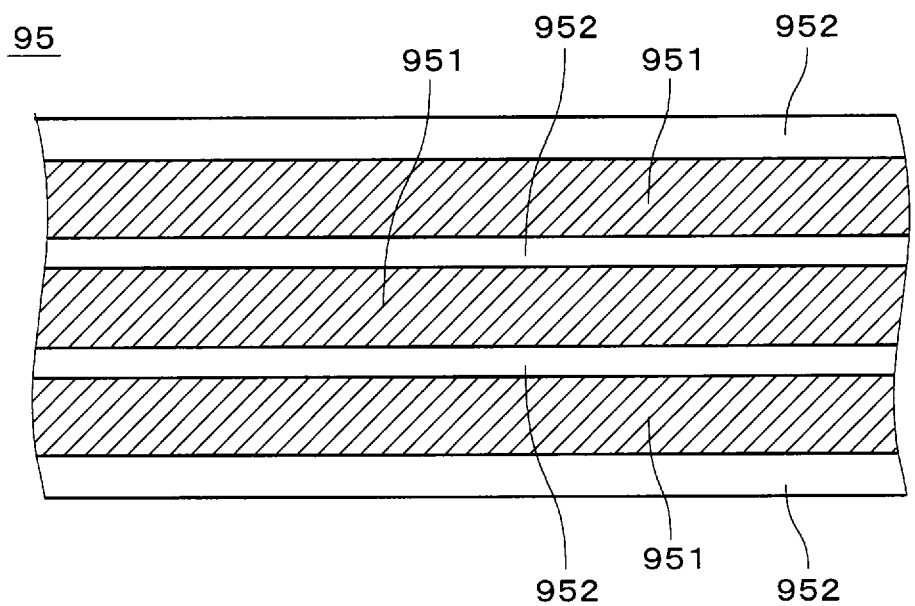
FIG. 8 is a plan view of an absorbent sheet.

This produces an absorbent sheet 95 in which a plurality of strip-like (or linear) particle existence regions 951 to which particles of the highly absorbent resin are applied and a plurality of strip-like (or linear) particle-free regions 952 where the first sheet member 91 and the second sheet member 92 are bonded to each other and there are substantially no particles are alternately arranged along the width of the sheet as shown in FIG. 8. In other words, the absorbent sheet 95 has a plurality of particle existence regions 951 formed in strips. In FIG. 8, the particle existence regions 951 are hatched with parallel diagonal lines.

Incidentally, with the absorbent sheet manufacturing apparatus 1 shown in FIG. 1, the weight of particles supplied onto the first sheet member 91 per unit time increases with increasing rotational speed (e.g., the number of revolutions per unit time) of the cylinder rotation mechanism 25, and the weight of particles supplied onto the first sheet member 91 per unit time decreases with decreasing rotational speed of the cylinder rotation mechanism 25. If the conveying speed of the first sheet member 91 by the first sheet conveying mechanism 30 is increased while the rotational speed of the cylinder rotation mechanism 25 is kept constant, the weight of particles supplied from the supply cylinder 21 to the first sheet member 91 per unit area, i.e., the density of particles on the first sheet member 91 decreases. If the conveying speed of the first sheet member 91 by the first sheet conveying mechanism 30 is reduced while the rotational speed of the cylinder rotation mechanism 25 is kept constant, the density of particles on the first sheet member 91 increases. With the absorbent sheet manufacturing apparatus 1, various changes can be made to the density of particles on the first sheet member 91 by the control part 71 controlling the cylinder rotation mechanism 25 and the first sheet conveying mechanism 30 to change the rotational speed of the cylinder rotation mechanism 25 and the conveying speed of the first sheet member 91.

Figure 9:
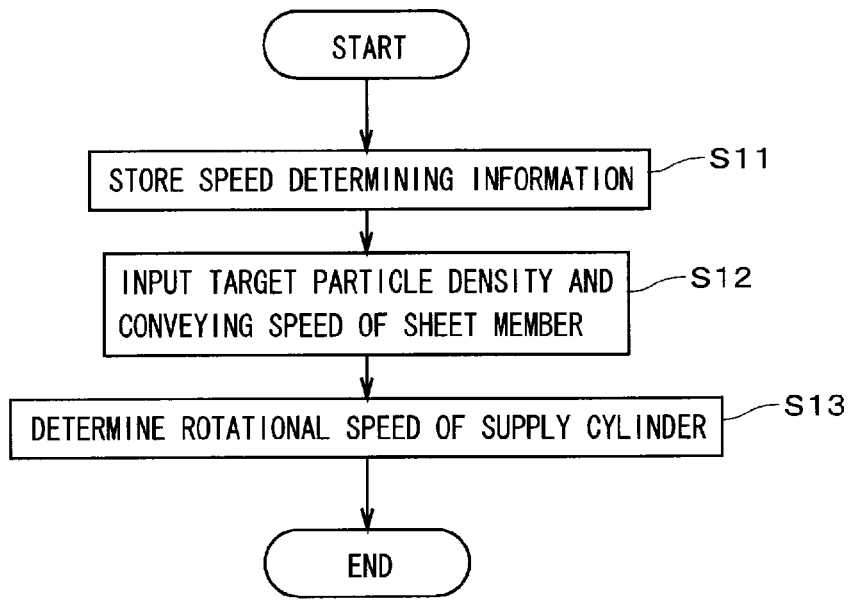
FIG. 9 is a flowchart of control performed by a control part.

FIG. 9 is a flowchart of control performed by the control part 71 when the absorbent sheet 95 (see FIG. 8) is manufactured by the absorbent sheet manufacturing apparatus 1 in FIG. 1. In the absorbent sheet manufacturing apparatus 1, a target particle density that is a target density of particles on the first sheet member 91 is first stored in the storage part 72, and a relationship between the conveying speed of the first sheet member 91 and the rotational speed of the supply cylinder 21 and corresponding to the target particle density is also stored in the storage part 72. In other words, the target particle density and a plurality of combinations of the conveying speed of the first sheet member 91 and the rotational speed of the supply cylinder 21 that make it possible to attain the target particle density are stored in the storage part 72. The storage part 72 stores not only a single target particle density but also a plurality of target particle densities and stores a plurality of relationships between the conveying speed of the first sheet member 91 and the rotational speed of the supply cylinder 21 for each of the target particle densities (step S11). In the following description, information that includes such relationships stored in the storage part 72 is referred to as "speed determining information." A method of acquiring the speed determining information will be described later.

Figure 10:
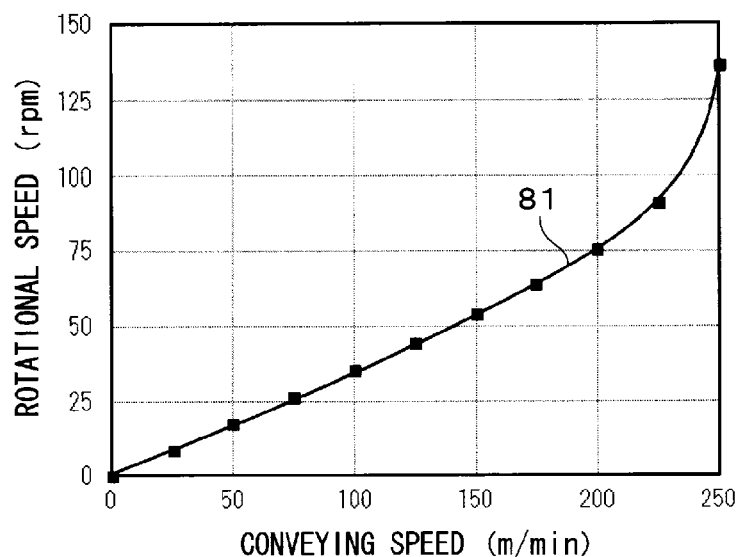
FIG. 10 shows a relationship between conveying speed of a first sheet member and rotational speed of the supply cylinder.

FIG. 10 shows the relationship between the conveying speed of the first sheet member 91 and the rotational speed of the supply cylinder 21, the relationship corresponding to one of the target particle densities included in the speed determining information. In FIG. 10, the horizontal axis indicates the conveying speed of the first sheet member 91, and the vertical axis indicates the rotational speed of the supply cylinder 21. A solid line 81 in FIG. 10 indicates that the rotational speed of the supply cylinder 21 gradually increases with increasing conveying speed of the first sheet member 91. The ratio of an increase in the rotational speed of the supply cylinder 21 to an increase in the conveying speed of the first sheet member 91 also gradually increases with increasing conveying speed of the first sheet member 91. In other words, the gradient of the solid line 81 gradually increases as the conveying speed of the first sheet member 91 increases.

The same applies to the relationships between the conveying speed of the first sheet member 91 and the rotational speed of the supply cylinder 21 that correspond respectively to the other target particle densities in the speed determining information. That is, both of the rotational speed of the supply cylinder 21 and the ratio of an increase in the rotational speed of the supply cylinder 21 to an increase in the conveying speed of the first sheet member 91 gradually increase with increasing conveying speed of the first sheet member 91.

With the absorbent sheet manufacturing apparatus 1 shown in FIG. 1, a target particle density for the absorbent sheet 95 to be manufactured and a conveying speed of the first sheet member 91 to be used in manufacturing the absorbent sheet 95 are input from the input part 73 and transmitted to the control part 71 (step S12). The control part 71 determines the rotational speed of the supply cylinder 21 to be used in manufacturing the absorbent sheet 95, on the basis of the target particle density, the conveying speed of the first sheet member 91, and the speed determining information that is stored in advance in the storage part 72 (step S13). Specifically, the relationship between the conveying speed of the first sheet member 91 and the rotational speed of the supply cylinder 21 and corresponding to the target particle density, which has been input in step S12, is extracted from the speed determining information stored in the storage part 72 in step S11. Then, the rotational speed of the supply cylinder 21 corresponding to the conveying speed of the first sheet member 91 that has been input in step S12 is determined on the basis of the extracted relationship.

When the rotational speed of the supply cylinder 21 has been determined, the control part 71 controls the first sheet conveying mechanism 30 such that the first sheet member 91 moves in the conveyance direction at the conveying speed that has been input in step S12. The control part 71 also controls the cylinder rotation mechanism 25 such that the supply cylinder 21 rotates at the rotational speed determined in step S13 to supply particles onto the first sheet member 91 that is being conveyed. The density of particles on the first sheet member 91 is equal to the target particle density that has been input in step S12. The first sheet member 91 and the second sheet member 92 are thereafter bonded to each other as described above, producing the absorbent sheet 95.

If, in the absorbent sheet manufacturing apparatus 1, the conveying speed of the first sheet member 91 is increased for the purpose of improving production efficiency in the manufacture of the absorbent sheet 95, steps S12 and S13 described above are performed to determine a higher rotational speed of the supply cylinder 21. Likewise, if the conveying speed of the first sheet member 91 is reduced, steps S12 and S13 are performed as well to determine a lower rotational speed of the supply cylinder 21. In this way, when the target particle density is not changed by changing the conveying speed, input of a target particle density in step S12 may be omitted, and the relationship between the conveying speed of the first sheet member 91 and the rotational speed of the supply cylinder 21, used at the time of previous determination of the rotational speed of the supply cylinder 21 may be used in step S13.

Steps S12 and S13 described above are also performed when the target particle density is changed for the purpose of, for example, changing the type (e.g., size or application) of the absorbent sheet 95. In this case, the rotational speed of the supply cylinder 21 that allows the new target particle density to be attained is determined.

As described above, with the absorbent sheet manufacturing apparatus 1, the speed determining information including a plurality of relationships between the conveying speed of the first sheet member 91 and the rotational speed of the supply cylinder 21 and corresponding respectively to a plurality of target particle densities is stored in the storage part 72. The control part 71 then determines the rotational speed of the supply cylinder 21 on the basis of the stored speed determining information, and the target particle density and the conveying speed of the first sheet member 91 that have been input from the input part 73. Accordingly, even if various changes are made to the conveying speed of the first sheet member 91, the amount of particles supplied can be controlled with high accuracy such that the density of particles on the first sheet member 91 matches the target particle density. Besides, even if various changes are made to the target particle density, the amount of particles supplied can be controlled with high accuracy in consideration of the conveying speed of the first sheet member 91 such that the density of particles on the first sheet member 91 matches the target particle density.

According to the aforementioned relationships between the conveying speed of the first sheet member 91 and the rotational speed of the supply cylinder 21 and corresponding to the respective target particle densities, both of the rotational speed of the supply cylinder 21 and the ratio of an increase in the rotational speed of the supply cylinder 21 to an increase in the conveying speed of the first sheet member 91 gradually increase with increasing conveying speed of the first sheet member 91. With the absorbent sheet manufacturing apparatus 1, the rotational speed of the supply cylinder 21 is determined on the basis of such relationships. This makes it possible to accurately control the amount of particles supplied and to cause the density of particles on the first sheet member 91 to substantially match the target particle density, irrespective of whether the conveying speed of the first sheet member 91 is relatively low or high.

If the type of the absorbent sheet 95 to be manufactured by the absorbent sheet manufacturing apparatus 1 is changed, the type of particles to be supplied onto the first sheet member 91 may be changed as well. If the type of particles is changed to particles having a different diameter or different hardness, for example, the density of particles to be supplied onto the first sheet member 91 may change even if the conveying speed of the first sheet member 91 and the rotational speed of the supply cylinder 21 remain unchanged.

In view of this, in the absorbent sheet manufacturing apparatus 1, the speed determining information stored in the storage part 72 also includes, for each of a plurality of types of particles, a plurality of relationships between the conveying speed of the first sheet member 91 and the rotational speed of the supply cylinder 21 and corresponding respectively to a plurality of target particle densities as described above. The rotational speed of the supply cylinder 21 is determined on the basis of this speed determining information, and the target particle density and the conveying speed of the first sheet member 91 that have been input from the input part 73. Accordingly, even if various changes are made to the type of particles, the amount of particles supplied can be controlled with high accuracy such that the density of particles on the first sheet member 91 matches the target particle density.

Figure 11:
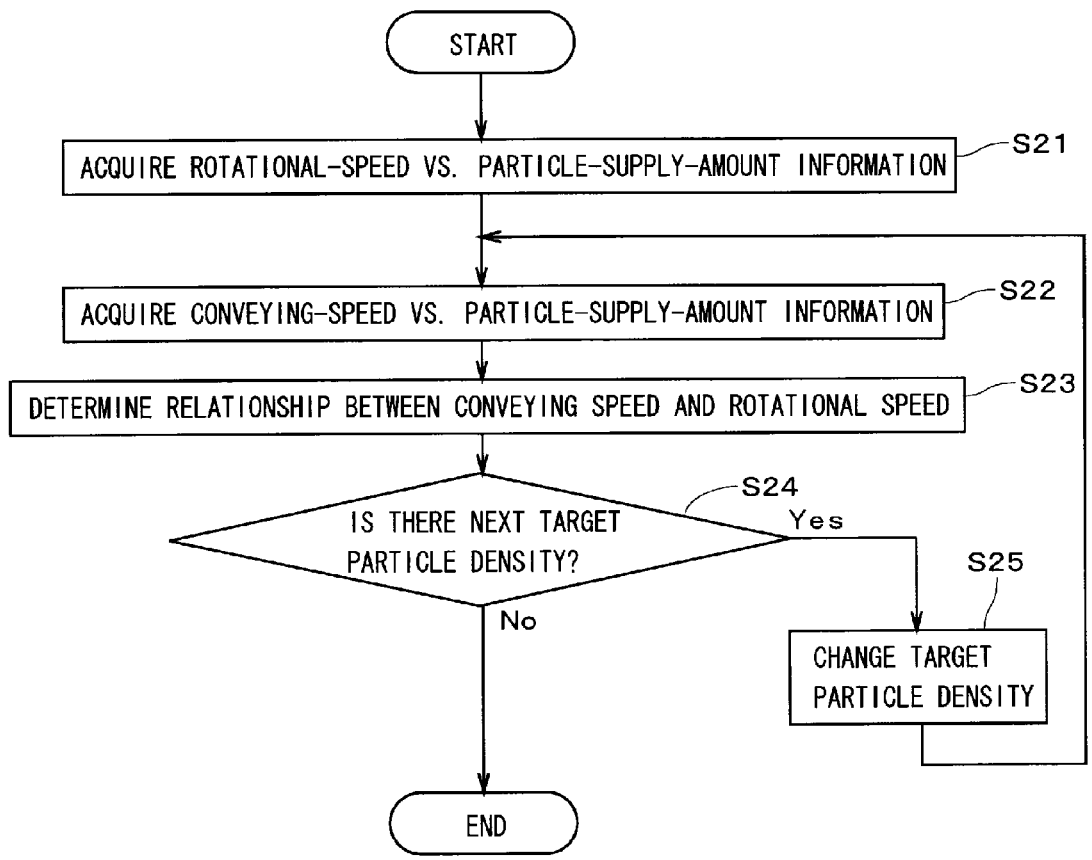
FIG. 11 is a flowchart showing a method of acquiring speed determining information.

FIG. 11 is a flowchart showing a method of acquiring the speed determining information used in the absorbent sheet manufacturing apparatus 1. In acquiring the speed determining information, first, the rotational speed of the supply cylinder 21 is kept constant and the amount of particles supplied from the supply cylinder 21 to the first sheet member 91 per unit time (i.e., the amount of particles supplied per unit time) is measured. Then, the rotational speed of the supply cylinder 21 is changed and the measurement of the amount of particles supplied per unit time is repeated. As a result, the amounts of particles supplied from the supply cylinder 21 to the first sheet member 91 per unit time are acquired for a plurality of rotational speeds of the supply cylinder 21, which yields rotational-speed vs. particle-supply-amount information shown in FIG. 12 (step S21).

Figure 13:
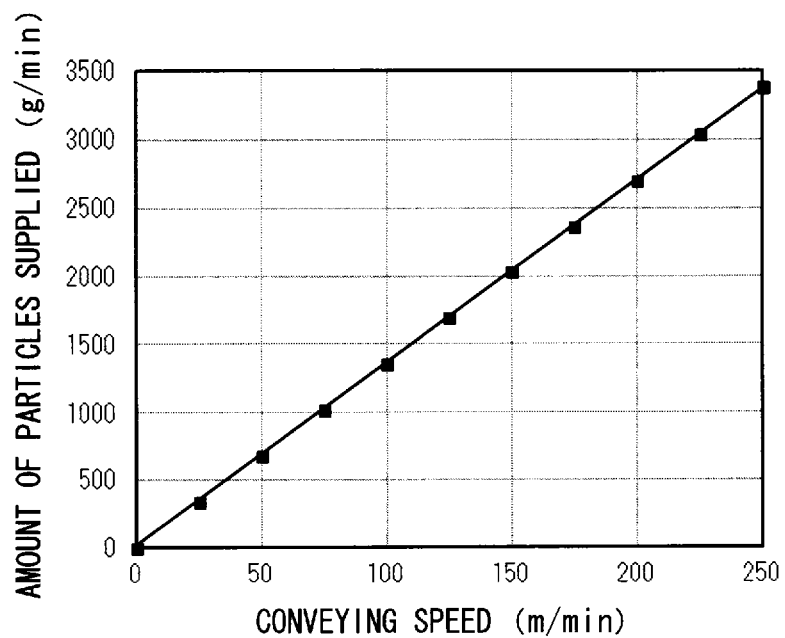
FIG. 13 shows conveying-speed vs. particle-supply-amount information.

Next, the amount of particles that is necessary to be supplied from the supply cylinder 21 per unit time in order to attain one target particle density is obtained for a plurality of conveying speeds of the first sheet member 91, which yields conveying-speed vs. particle-supply-amount information shown in FIG. 13 (step S22).

Figure 12:
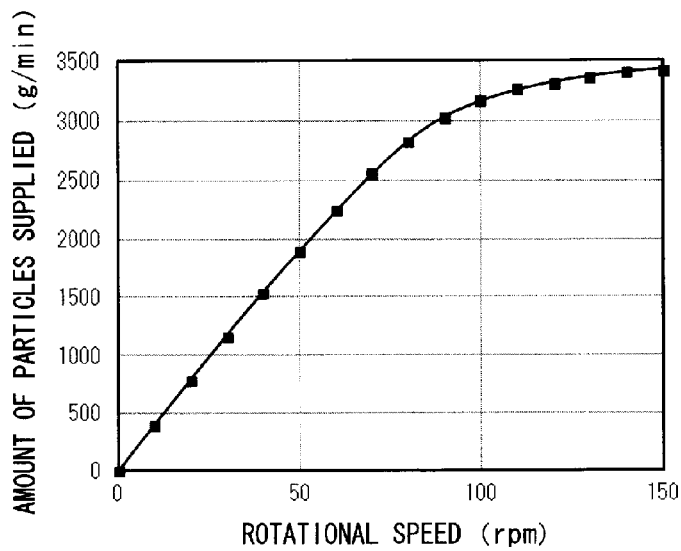
FIG. 12 shows rotational-speed vs. particle-supply-amount information.

Then, the relationship between the conveying speed of the first sheet member 91 and the rotational speed of the supply cylinder 21 and corresponding to the aforementioned target particle density is obtained as shown in FIG. 10 on the basis of the rotational-speed vs. particle-supply-amount information in FIG. 12 and the conveying-speed vs. particle-supply-amount information in FIG. 13 (step S23).

After that, the target particle density is changed (steps S24 and S25), and steps S22 and S23 are performed for the new target density to obtain the relationship between the conveying speed of the first sheet member 91 and the rotational speed of the supply cylinder 21 and corresponding to the new target particle density. The absorbent sheet manufacturing apparatus 1 repeatedly performs steps S22 to S25 for a plurality of target particle densities. As a result, a plurality of relationships between the conveying speed of the first sheet member 91 and the rotational speed of the supply cylinder 21 and corresponding respectively to the plurality of target particle densities are acquired and stored as the speed determining information in the storage part 72.

With the above-described acquisition method, the absorbent sheet manufacturing apparatus 1 can easily acquire highly precise speed determining information. Using the acquired speed determining information to determine the rotational speed of the supply cylinder 21 in the manufacture of the absorbent sheet 95 allows the absorbent sheet manufacturing apparatus 1 to accurately control the amount of particles supplied such that the density of particles on the first sheet member 91 matches the target particle density.

While the above has been a description of embodiments of the present invention, the present invention is not limited to the embodiments described above, and can be modified in various ways.

For example, the relationship between the conveying speed of the first sheet member 91 and the rotational speed of the supply cylinder 21 and corresponding to a target particle density in the above speed determining information may exhibit a different characteristic from that indicated by the solid line 81 in FIG. 10. For example, the ratio of an increase in the rotational speed of the supply cylinder 21 to an increase in the conveying speed of the first sheet member 91 may be constant when the conveying speed of the first sheet member 91 is less than a predetermined threshold value, and the ratio of an increase in the rotational speed of the supply cylinder 21 to an increase in the conveying speed of the first sheet member 91 may gradually increase with increasing conveying speed of the first sheet member 91 when the conveying speed of the first sheet member 91 is greater than or equal to the above threshold value.

If the absorbent sheet manufacturing apparatus 1 uses only one type of particles to manufacture the absorbent sheet 95, it is not necessary to include, for the other types of particles, a plurality of relationships between the conveying speed of the first sheet member 91 and the rotational speed of the supply cylinder 21 and corresponding respectively to a plurality of target particle densities in the speed determining information. The absorbent sheet manufacturing apparatus 1 may use various methods other than the above-described acquisition method (steps S21 to S25) to acquire the speed determining information.

If the recessed supply portions 212 are replenished with particles in sufficiently high density, the particle replenishment opening 232 does not necessarily have to be disposed to face the area including the uppermost portion of the supply cylinder 21, and may be disposed to face a portion of the supply cylinder 21 that is posterior to or anterior to the uppermost portion in the rotation direction.

While the above embodiment describes the manufacture of the absorbent sheet 95 in which the particle existence regions 951 are formed in strips, the absorbent sheet manufacturing apparatus 1 may manufacture, for example, an absorbent sheet in which particle existence regions are formed in dots by increasing the intervals in the circumferential direction between the recessed supply portions 212 of the supply cylinder 21.

The supply cylinder 21, the cylinder rotation mechanism 25, the first sheet conveying mechanism 30, the first cover part 221, the second cover part 222, the particle replenishment part 23, the control part 71, the storage part 72, and the input part 73, which are described above, may be incorporated into various apparatuses other than the absorbent sheet manufacturing apparatus 1, as a particle supplying apparatus 10 (see FIG. 1) for supplying particles of an absorbent material onto a sheet member. For example, a configuration is possible in which the first sheet conveying mechanism 30 conveys a sheet member having an upper surface to which pulp fiber or the like has been supplied, and the supply cylinder 21 supplies particles of a highly absorbent resin onto the pulp fiber. In this case, particles in the recessed supply portions 212 can be mixed with the pulp fiber.

With the above-described particle supplying apparatus 10, particles of an absorbent material such as partially neutralized and crosslinked polyacrylic acid, hydrolyzed starch-acrylic acid graft polymer, saponified vinyl acetate-acrylic ester copolymer, hydrolyzed acrylonitrile copolymer, crosslinked acrylonitrile copolymer, hydrolyzed acrylamide copolymer, crosslinked acrylamide copolymer, crosslinked cationic monomers, or crosslinked polyamino acid are supplied onto a sheet member. Alternatively, the particle supplying apparatus 10 may be used as an apparatus for supplying particles of a deodorant material such as activated carbon, silica, alumina, zeolite, an ion-exchange resin, or molecular sieve onto a sheet member. In this case, with an absorbent-article sheet member manufacturing apparatus provided with the particle supplying apparatus 10, particles of the deodorant material held in the particle replenishment part 23 are charged into the recessed supply portions 212 of the supply cylinder 21 and supplied onto a sheet member so as to manufacture a deodorant sheet, which is an absorbent-article sheet member, for absorbent articles such as disposable diapers or absorbent pads for light incontinence.

The configurations of the above-described preferred embodiments and variations may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention. This application claims priority benefit under 35 U.S.C. Section 119 of Japanese Patent Application No. 2012-224052 filed in the Japan Patent Office on Oct. 9, 2012, the entire disclosure of which is incorporated herein by reference.

REFERENCE SIGNS LIST

1 Absorbent sheet manufacturing apparatus
10 Particle supplying apparatus
21 Supply cylinder
23 Particle replenishment part
25 Cylinder rotation mechanism
30 First sheet conveying mechanism
71 Control part
72 Storage part
73 Input part
91 First sheet member
211 Cylinder outer side surface
212 Recessed supply portions
232 Particle replenishment opening
R1 Cylinder rotational axis
S11 to S13, S21 to 25 Step

The invention claimed is:

1. A particle supplying apparatus for supplying particles of an absorbent material or a deodorant material onto a sheet member, comprising:

a supply cylinder having a cylinder outer side surface having a plurality of recessed supply portions arranged in a circumferential direction;

a particle replenishment part located above said supply cylinder, containing particles of an absorbent material or a deodorant material, and for successively replenishing said plurality of recessed supply portions with the particles through a particle replenishment opening that faces said cylinder outer side surface;

a sheet conveying mechanism located below said supply cylinder and for conveying a sheet member that is a continuous sheet in a predetermined conveyance direction;

a cylinder rotation mechanism for rotating said supply cylinder about a cylinder rotational axis extending in a horizontal direction and bringing a lower portion of said cylinder outer side surface and said sheet member into contact with or close proximity to each other so as to successively supply the particles from said plurality of recessed supply portions onto said sheet member;

a storage part for storing speed determining information that includes a plurality of relationships between conveying speed of said sheet member and rotational speed of said supply cylinder and corresponding respectively to a plurality of target particle densities that are target densities of the particles on said sheet member;

an input part; and a control part for determining a rotational speed of said supply cylinder on the basis of a target particle density and a conveying speed of said sheet member that are input from said input part and said speed determining information stored in said storage part.

2. The particle supplying apparatus according to claim 1, wherein
said speed determining information includes, for each of a plurality of types of particles, a plurality of relationships between conveying speed of said sheet member and rotational speed of said supply cylinder and corresponding respectively to said plurality of target particle densities.

3. The particle supplying apparatus according to claim 2, wherein
in each of said plurality of relationships between conveying speed of said sheet member and rotational speed of said supply cylinder, a ratio of an increase in the rotational speed of said supply cylinder to an increase in the conveying speed of said sheet member gradually increases with an increase in the conveying speed of said sheet member.

4. The particle supplying apparatus according to claim 1, wherein
in each of said plurality of relationships between conveying speed of said sheet member and rotational speed of said supply cylinder, a ratio of an increase in the rotational speed of said supply cylinder to an increase in the conveying speed of said sheet member gradually increases with an increase in the conveying speed of said sheet member.

* * * * *